United States Patent [19]
Godec et al.

[11] Patent Number: 5,750,073
[45] Date of Patent: May 12, 1998

[54] REAGENTLESS OXIDATION REACTOR IN A CARBON MEASURING SYSTEM

[75] Inventors: Richard D. Godec, Longmont; Paul P. Kosenka; Richard S. Hutte, both of Boulder, all of Colo.

[73] Assignee: Sievers Instruments, Inc., Boulder, Colo.

[21] Appl. No.: 263,610

[22] Filed: Jun. 20, 1994

Related U.S. Application Data

[60] Continuation-in-part of Ser. No. 869,308, Apr. 16, 1992, Pat. No. 5,443,991, which is a division of Ser. No. 487,720, Mar. 2, 1990, Pat. No. 5,132,094.

[51] Int. Cl.$^6$ .......................... G01N 31/12; G01N 33/00
[52] U.S. Cl. .................. 422/79; 422/78; 422/80; 422/82.01; 422/82.04; 436/145; 436/146
[58] Field of Search ................. 422/22, 24, 76, 422/78, 79, 80, 82.01–82.04; 436/145, 146, 150, 151, 128–134, 126; 204/129, 412, 413; 210/259, 321.75, 321.84, 748, 758, 759

[56] References Cited

U.S. PATENT DOCUMENTS

| | | |
|---|---|---|
| 3,925,212 | 12/1975 | Tchernev .................. 204/129 |
| 4,293,522 | 10/1981 | Winkler . |
| 4,547,273 | 10/1985 | Ayers ...................... 204/73 R |
| 4,619,902 | 10/1986 | Bernard . |
| 4,626,413 | 12/1986 | Blades ........................ 422/78 |
| 5,132,094 | 7/1992 | Godec et al. ............... 422/68.1 |
| 5,443,991 | 8/1995 | Godec et al. ............... 436/145 |

Primary Examiner—Arlen Soderquist
Attorney, Agent, or Firm—Lappin & Kusmer LLP

[57] ABSTRACT

An oxidation reactor having particular utility in a system for measuring carbon in an aqueous sample. A first chamber and second chamber are separated by a hydrogen-permeable electrode, each chamber having a separate electrolysis cell. The hydrogen-permeable electrode acts as the anode of one cell and the cathode of the other cell. The sample stream flows into one chamber and the electrolysis cell produces oxygen from the water at one optically transparent electrode and in combination with short wave ultraviolet light oxidizes organic carbon to $CO_2$ and produces hydrogen at the other electrode which passes through the hydrogen-permeable electrode into the second chamber. The electrolysis cell in the second chamber produces oxygen at hydrogen-permeable electrode to react with the hydrogen that passes through the hydrogen-permeable electrode to form water, thereby maintaining the maximum concentration gradient of hydrogen across the hydrogen-permeable electrode to improve hydrogen transferring efficiency.

43 Claims, 5 Drawing Sheets

REAGENTLESS OXIDATION REACTOR IN A CARBON MEASURING SYSTEM

This is a continuation-in-part of application Ser. No. 07/869,308 filed Apr. 16, 1992, now issued as U.S. Pat. No. 5,443,991, which is a divisional application of application Ser. No. 07/487,720 filed Mar. 2, 1990, now issued as U.S. Pat. No. 5,132,094.

FIELD OF THE INVENTION

The present invention relates to an improved method and apparatus for the in-situ generation of oxidizing agents used in conjunction with photo-oxidation of organic compounds to form carbon dioxide, and the use of the same in the determination of the total concentration of organic and/or inorganic carbon compounds in aqueous process streams and in bulk solutions.

BACKGROUND OF THE INVENTION

The measurement of the total organic carbon (TOC) concentration and total carbon concentration in water has become a standard method for ascertaining the level of contamination by organic compounds in potable waters, industrial process waters, and municipal and industrial waste waters. In addition to widespread terrestrial applications, the measurement of TOC is one of the primary means for determining the purity of potable and process waters for manned space based systems including the space shuttle, the proposed space station and for future manned explorations of the moon and other planets.

A variety of prior art approaches for measuring the total organic carbon content of water have been proposed. For example, see U.S. Pat. Nos. 3,958,941 of Regan; 3,224,837 of Moyat; 4,293,522 of Winkler; 4,277,438 of Ejzak; 4,626,413 and 4,666,860 of Blades et. al.; and 4,619,902 of Bernard.

Representative of the devices described in these references are the methods disclosed in U.S. Pat. No. 3,958,941 of Regan. In Regan an aqueous sample is introduced into a circulating water stream that flows through a reaction chamber where the sample is mixed with air and exposed to ultraviolet (U.V.) radiation to promote the oxidation of organic compounds to form carbon dioxide. The carbon dioxide formed in the reaction chamber is then removed from solution by an air stripping system and introduced into a second chamber containing water that has been purified to remove ionic compounds. The conductivity of the water in the second chamber is measured, and any increase in conductivity is related to the concentration of carbon dioxide formed in the first reactor. The conduction measurement can be used, therefore, to determine the concentration of organic compounds in the original sample.

The Regan device is slow, cannot be used for the continuous monitoring of TOC concentration in aqueous streams, cannot be scaled down without increasing interference from $NO_2$, $SO_2$ and $H_2S$ to unacceptable levels, and is generally unsatisfactory. In addition, Regan does not disclose that an aqueous solution of acid must be added to the sample stream to reduce the pH to a value of less than about 4 to insure a reasonable removal rate of carbon dioxide using the air stripping system described. The oxidation method disclosed by Regan is unsatisfactory for the measurement of refractory compounds, particularly urea. In Regan, an aqueous sample of 20 to 100 mL containing 0.5 mg/L organic carbon is required to generate sufficient carbon dioxide for accurate detection, thus limiting the utility of the device for the measurement of sub-part per million levels of TOC in smaller sample sizes. Finally, in practice, the Regan system requires frequent recalibration—typically once per day—due to variations in background conductivity. Also, the concentration of total organic carbon in the calibration standard must be approximately equal to the concentration of organic carbon in the sample. Because of this, recalibration is required when analyzing aqueous samples containing higher or lower levels of organic carbon when compared with the calibration standard.

An improved method and apparatus for the measurement of organic content of aqueous samples is that disclosed in U.S. Pat. No. 4,277,438 of Ejzak. Ejzak describes a multi-stage reactor design which provides for the addition of oxygen and a chemical oxidizing agent, preferably sodium persulfate, to the aqueous sample stream prior to oxidation of the stream using ultraviolet radiation in a series of reactors. Ejzak also describes the use of an inorganic carbon stripping process—before oxidation of the organic carbon—that includes the addition of phosphoric acid to the sample stream. After oxidation, the sample stream is passed into a gas-liquid separator where the added oxygen acts as a carrier gas to strip carbon dioxide and other gases from the aqueous solution. In the preferred embodiment, the gas stream is then passed through an acid mist eliminator, a coalescer and salt collector, and through a particle filter prior to passage into an infrared (IR) detector for the measurement of the concentration or carbon dioxide in the gas stream.

The methods and apparatus disclosed by Ejzak provide improvements over the teachings of Regan; however, the Ejzak device requires extensive manual operation and is also generally unsatisfactory. The Ejzak device requires three external chemical reagents: oxygen gas, aqueous phosphoric acid and an aqueous solution of sodium persulfate. Both the phosphoric acid and persulfate solutions must be prepared at frequent intervals by the operator due to the relatively high rate of consumption. The Ejzak device requires dilution of the sample if the solution contains high concentrations of salts in order to insure complete oxidation of the sample and to eliminate fouling of the particle filter located prior to the IR carbon dioxide detector. As with Regan, relatively large sample sizes are required—typically 20 mL of sample for accurate measurement at 0.5 mg/L total organic carbon—and the carbon dioxide formed in the oxidation chamber is removed using a gravity dependent technique that cannot be easily used in space-based operations.

Another improved method and apparatus for the measurement of total organic carbon in water is disclosed in U.S. Pat. No. 4,293,522 of Winkler. In Winkler, an oxidizing agent, molecular oxygen, is generated in-situ by the electrolysis of water. Organic compounds are subsequently oxidized to form carbon dioxide by the combination of U.V. radiation and the in-situ generated oxygen. The irradiation and electrolysis processes are both accomplished in a single oxidation chamber. Winkler does not teach that the aqueous sample stream be acidified to assist in the removal of carbon dioxide from solution, and in fact teaches against the use of acid. Therefore, this method and apparatus cannot be used for the measurement of organic compounds in basic aqueous samples. The oxidation chamber of Winkler uses a solid electrolyte to separate the two electrodes employed for the electrolysis of water. The solid electrolyte described by Winkler is composed of an organic polymer which, under exposure to oxygen, ozone and U.V. radiation, will undergo oxidation to form carbon dioxide, therefore resulting in unacceptable background levels of organic compounds in the sample stream, particularly at low organic compound concentrations.

Winkler also describes a conductometric carbon dioxide detection system wherein the sample stream exiting the oxidizing chamber is held in an equilibrating relationship to a stream of deionized water. The two flowing streams are separated by a gas permeable membrane that allows the concentration of carbon dioxide to equilibrate between the streams. The concentration of the carbon dioxide is thereby determined by measuring the conductance of the deionized water stream. However, the use of two flowing streams introduces operating parameters into the detection process that require frequent calibration adjustments.

Another example of the prior art is that disclosed in U.S. Pat. No. 4,619,902 of Bernard, which teaches the oxidation of organic compounds to form carbon dioxide using persulfate oxidation at elevated temperatures—typically 20° to 100° C.—in the presence of a platinum metal catalyst. Bernard recognizes that the materials used in the construction of instrumentation for the determination of total organic carbon in water can contribute organic compounds to the sample during the measurement process, and teaches that inert materials such as PTFE must be used to reduce this background from the measurement. As with the previously mentioned disclosure, a gas stripping technique is employed to collect the formed carbon dioxide, and measurement is made using IR spectrometry. Bernard also recognizes that aqueous solutions of sodium persulfate are not stable due to auto-degradation of the reagent.

An improved system for the measurement of organic compounds in deionized water is disclosed in U.S. Pat. No. 4,626,413 of Blades and Godec. The apparatus described by Blades and Godec is based on direct U.V. oxidation of organic compounds to form carbon dioxide which is measured by using conductometric detection. In the apparatus described in Blades and Godec, the oxidation of some organic compounds form strong acids such as HCl, $H_2SO_4$ and $HNO_3$ which interfere with the conductometric method. The Blades device is also limited to the measurement of total organic compounds in deionized water and cannot be used for samples containing ionic compounds other than bicarbonate ion.

In U.S. Pat. No. 4,209,299 of Carlson, it is disclosed that the concentration of volatile materials in a liquid can be quantitatively determined by transferring the desired material through a gas permeable membrane into a liquid of known conductivity, such as deionized water. The Carlson device is demonstrated for the measurement of a number of volatile organic and inorganic compounds, but Carlson does not suggest the combination of this process in conjunction with a carbon dioxide producing reactor.

The use of aqueous solutions of persulfate salts for the oxidation of organic compounds is widely known. Smit and Hoogland (16 Electrochima Acta, 1–18 (1971)) demonstrate that persulfate ions and other oxidizing agents can be electrochemically generated.

In U.S. Pat. No. 4,504,373 of Mani et. al., a method for the electrochemical generation of acid and base from aqueous salt solutions is disclosed.

In electrochemical reactions in aqueous solutions, a common reduction product is hydrogen gas. Because of its flammability, the hydrogen presents a potential hazard in devices using electrochemical techniques. The interaction of hydrogen gas in aqueous solutions and palladium metal is well known (e.g., F. A. Lewis, "The Palladium Hydrogen System, " Academic Press, 1967, London, incorporated herein by this reference) and the use of palladium offers a potential solution to the generation of hydrogen in electrochemical reactions by selective removal and disposal of the hydrogen.

In U.S. Pat. No. 5,132,094, of which the present is a continuation-in-part, many of the prior art limitations are overcome. That patent discloses an apparatus and method using a selective carbon dioxide-permeable membrane for the transport of carbon dioxide from either an oxidized or unoxidized sample stream into a second aqueous solution where the sensitive detection of carbon dioxide is accomplished using conductometric measurement, thus eliminating the use of a gas stripping apparatus. That patent also employs in-situ generation of oxidizing agents including persulfate ions, hydrogen peroxide and molecular oxygen, thus eliminating the need for the introduction of gases and unstable chemical reagents; an in-line acidification module which permits accurate determination of the organic content of aqueous samples over a wide sample pH range; and the incorporation of an oxidation catalyst to insure rapid and complete photo-oxidation of organic compounds.

SUMMARY OF THE INVENTION

In one embodiment of the present invention, an aqueous sample stream is passed through a filter to remove any particulate matter, and passed into a acidification module for the introduction of a suitable concentration of acid to cause a reduction in the pH of the solution to a pH of less than 4. Inorganic carbon species—primarily carbonate and bicarbonate ions—are reacted with the acid to form carbon dioxide, while organic compounds remain unreacted.

The effluent of the acidification module is directed into an inorganic carbon removal module comprised of a carbon dioxide selective gas permeable membrane or a non-selective gas permeable membrane, which separates the acidified sample stream from a second aqueous stream in which the pH of the stream has been raised to a pH of greater than 10 by addition of a suitable base. The carbon dioxide formed from the reaction of inorganic carbon species with the acid will selectively diffuse across the gas permeable membrane into the basic aqueous stream where the carbon dioxide will be converted to ionic species (carbonate or bicarbonate) for subsequent disposal.

The acidic and basic streams used in the acidification module and inorganic carbon removal modules may be composed of aqueous solutions of suitable acids and bases or, alternatively, an aqueous salt solution can be passed through a system incorporating a bi-polar membrane (see U.S. Pat. No. 4,504,373, hereby incorporated herein by this reference) for the in-situ generation of an acidic stream, a basic stream, and a depleted salt stream.

The effluent of the inorganic carbon removal module is then directed into a U.V. oxidation module which incorporates direct U.V. oxidation using short wavelength U.V. radiation and U.V. oxidation in the presence of oxygen which is generated in-situ by the electrolysis of water. In the U.V. oxidation reactor, organic compounds are converted to carbon dioxide. A palladium cathode system can be employed in the electrolysis apparatus to remove the hydrogen generated during the electrolysis of water thereby producing a net increase of oxygen in the electrolysis cell.

The preferred embodiment utilizes a three electrode system: electrode #1 is an optically transparent wire screen anode of the primary oxidation electrolysis chamber, electrode #2 is a Pd/Ag alloy bi-electrode (connected to ground) and electrode #3 is a stainless steel cathode in the secondary electrolysis chamber. In the primary oxidation electrolysis chamber, oxidation of the organic compounds (and production of oxygen from water) occurs at and near the wire electrode #1 from the net increase of electrochemically generated oxygen in the presence of intense short wave ultraviolet light. Electrochemical reduction of water to form hydrogen occurs at the Pd/Ag electrode #2. On the back side of electrode #2, electrochemical oxidation of water to produce oxygen is the desired reaction, while electrochemical reduction of water to produce hydrogen occurs at electrode #3. Since the Pd/Ag alloy electrode is permeable to hydrogen, the goal is to have hydrogen produced in the primary oxidation reactor diffuse through the Pd/Ag alloy. At the metal/solution interface of the secondary electrolysis cell, the hydrogen atoms encounter oxygen, formed from electrolysis of water and are effectively removed at this interface from the system. The concentration of hydrogen is very close to zero in the secondary electrolysis chamber at electrode #2 to insure a high gradient across the interface.

The carbon dioxide formed in the photoreactor is then sensitively measured using a carbon dioxide sensor. The sensor is comprised of a carbon dioxide selective gas permeable membrane which separates the acidified sample stream from a deionized water reservoir. The deionized water is continuously generated by means of a mixed bed ion exchange resin. Alternatively, deionized water can be supplied from a source external to the apparatus described in the present invention.

In the basic measurement cycle, a fresh pulse of deionized water is introduced into the deionized water side of the gas permeable membrane and a shut-off valve actuated to stop the flow of deionized water. The effluent of the photoreactor continuously flows on the opposite side of the membrane. The carbon dioxide formed in the photoreactor from the oxidation of organic compounds diffuses across the gas permeable membrane until the concentration of carbon dioxide in the two aqueous streams is substantially the same. As the carbon dioxide enters the deionized water, the carbon dioxide will dissolve in the water and cause an increase in the conductivity of the aqueous solution. After equilibrium has been established (typically about 5 min. ), a fresh pulse of deionized water is introduced to sweep the equilibrated solution into a conductivity cell in order to measure the increase in the concentration of ionic species.

The increase in conductivity observed in the deionized water can be directly related to the concentration of carbon dioxide in the sample stream and hence the level of organic compounds originally present in the sample stream.

DETAILED DESCRIPTION OF THE INVENTION

Figure 1:
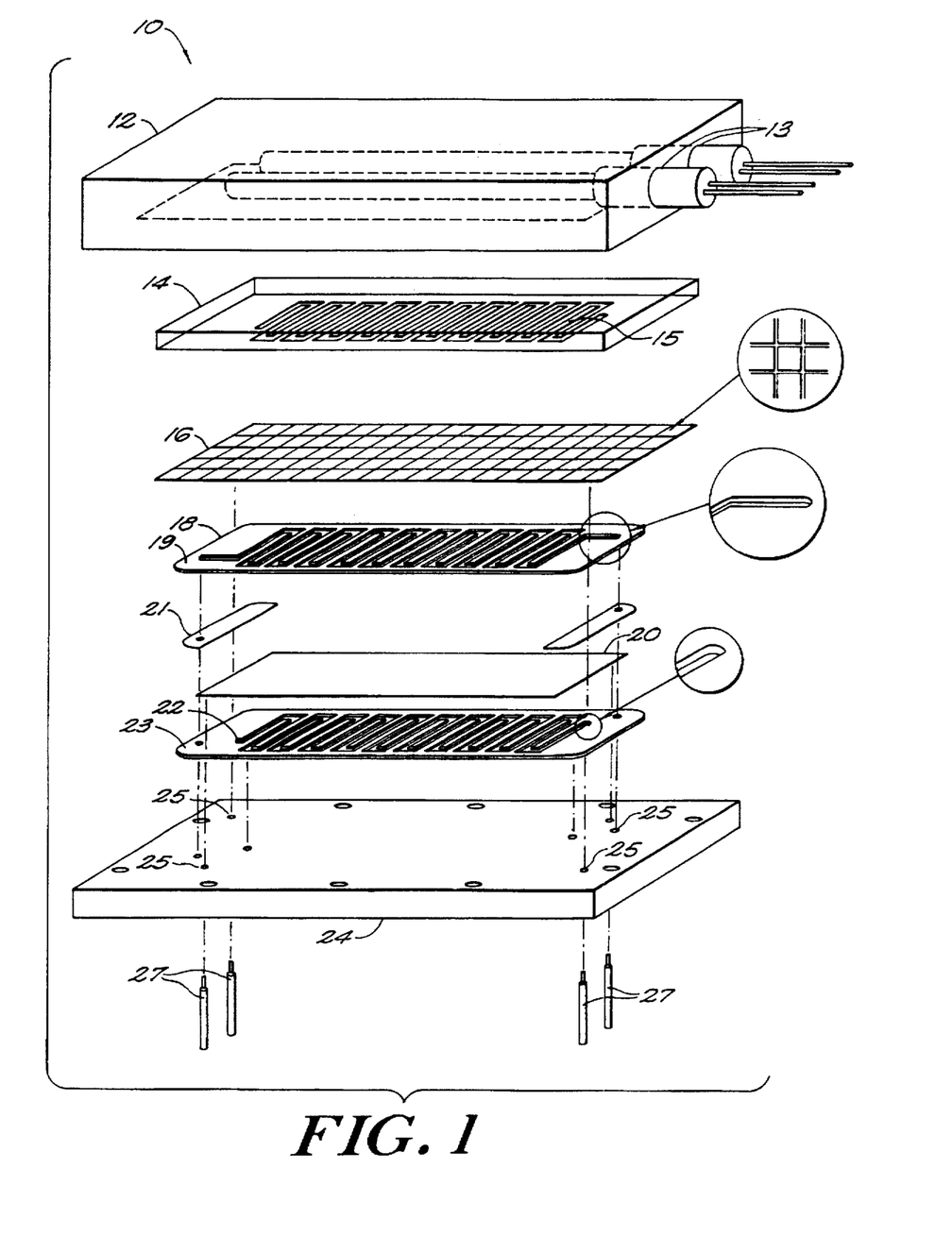
FIG. 1 is an exploded schematic view of the oxidation reactor of the present invention.

A schematic of the oxidation reactor 10 used in this study is shown in FIG. 1. There are seven basic components for the oxidation reactor: U.V. lamps and housing 12, fused silica window 14, wire-mesh anode 16 of titanium, platinum, gold or other suitable material, ceramic sample chamber 18, a bielectrode (which functions as a cathode in the primary oxidation electrolysis cell and an anode in the secondary electrolysis cell) 20, second ceramic sample chamber 22, and a stainless steel pressure plate 24. A more detailed description of these components is set forth below.

Two low-pressure mercury vapor lamps 13 are located in a stainless steel housing 12 positioned above the sample chamber 18. The lamps 13 emit radiation at both 254 nm and 184 nm. The short wavelength radiation produces hydroxyl radicals from the photolysis of water for the oxidation of organic compounds. The housing 12 is also equipped with a view port (not shown) to permit inspection of the inside of the reactor.

While these lamps are commonly used for photochemical oxidation, the lamps only emit a small fraction (~3%) of radiation in the short wavelength region (185 nm). Recently new lamps have been developed with high intensity emissions in the vacuum ultraviolet (175–210 nm), the wavelength region favorable for the formation of $O_3$, $H_2O_2$ and OH. Xenon-doped mercury lamps have a maximum intensity in the 210 to 230 nm region. Krypton chloride excimer lamps emit at 222±6 nm and Xenon excimer lamps have a maximum emission at 172±nm. The use of these UV sources in the oxidation reactor increases the amount of oxidizing agents produced photochemically and improves the oxidation efficiency compared with the Hg vapor lamps. Another advantage of these lamps compared with the Hg vapor unit, particularly for space-based applications, is the elimination of the toxic element mercury. To avoid potential leakage and exposure to Hg, triple containment systems are required for Hg vapor lamps. Using Xe excimer lamps eliminates these special containment requirements and provides more efficient generation of oxidizing agents.

A fused silica window 14 is located below the lamp 13 to provide a liquid-tight seal, yet permit transmission of the UV radiation to the sample chamber 18. To limit the exposure of UV radiation to the sample chamber 18 and avoid exposing other components of the reactor to UV, an anode mask formed from the deposition of a Pt alloy on the fused silica is employed. This thin layer of Pt alloy is deposited in a serpentine pattern identical to that of the sample chamber 18. The mask is not part of the electrical system, but simply limits the transmission of UV light to the sample chamber 18, preventing possible oxidation of other components of the reactor.

Positioned below the fused silica window 14 is the wire mesh anode 16. The anode is a flat piece, with the wire mesh formed by etching the metal, rather than weaving the wire. The wire anode in the preferred embodiment is 0.025 mm thick, with 0.23 mm×0.23 mm square holes etched into the metal to permit transmission of UV light to the sample chamber 18. Use of the wire anode provides electrochemical production of oxygen from water and combined with the intense short wave UV light provides for the oxidation of organic compounds.

A ceramic spacer 19 with a laser cut serpentine pattern is used to define the sample chamber 18 to contain the sample. The spacer in the preferred embodiment is composed of 99.9% $Al_2O_3$ and the serpentine flow channel is 2.1 mm wide×0.4 mm deep with a calculated volume of 0.76 mL.

Positioned below the sample chamber is the cathode 20. The cathode material in the preferred embodiment is a 0.13 mm thick Pd/Ag alloy (25% Ag). The cathode is electrically isolated from the stainless steel housing of the reactor by means of two TEFZEL brand from DuPont ethylene-tetraflouroethylene copolymer type material spacers 21.

Positioned below the cathode 20 is a sheet of TEFZEL brand from DuPont ethylene-tetraflouroethylene copolymer type material 23, 0.48 mm thick, with a serpentine pattern cut into the spacer. The second sample chamber 22 is filled with liquid and used as a second electrolysis cell. After the concentration of $CO_2$ in the outlet stream of the primary oxidation reactor is measured using the membrane-based $CO_2$ sensor, the waste stream is then passed back through the second sample chamber, as shown in the schematic drawing of FIG. 3. As will be described in more detail below, the waste stream is used to generate oxygen and hydrogen electrolytically. The goal is to rapidly remove hydrogen from the primary oxidation reactor by reacting it with oxygen produced in the second electrolysis cell.

The reactor is sealed by means of a stainless steel pressure plate 24 which also serves as one of the electrodes (cathode) for the second electrolysis cell. In order to provide a liquid tight seal throughout the reactor, it is necessary to use a small amount of TEFLON grease (DuPont KRYTOX brand). A minimal amount of the grease is applied to the surfaces between the components.

As shown in FIG. 1, the stainless steel pressure plate 24 and the spacer 21 are fitted with holes 25 to provide electrical contact to the cathode. Metal pins 27 are inserted through the holes at opposite edges of the pressure plate and contact the edges of the cathode. The wire anode 16 is slightly larger than the ceramic spacer 19 and cathode 20. The metal pins 27 can therefore be inserted through the pressure plate 24 (not touching it) to contact the wire anode 16 (again at opposite corners) without touching the cathode 20 to provide the electrical contact to the anode 16.

Figure 2:
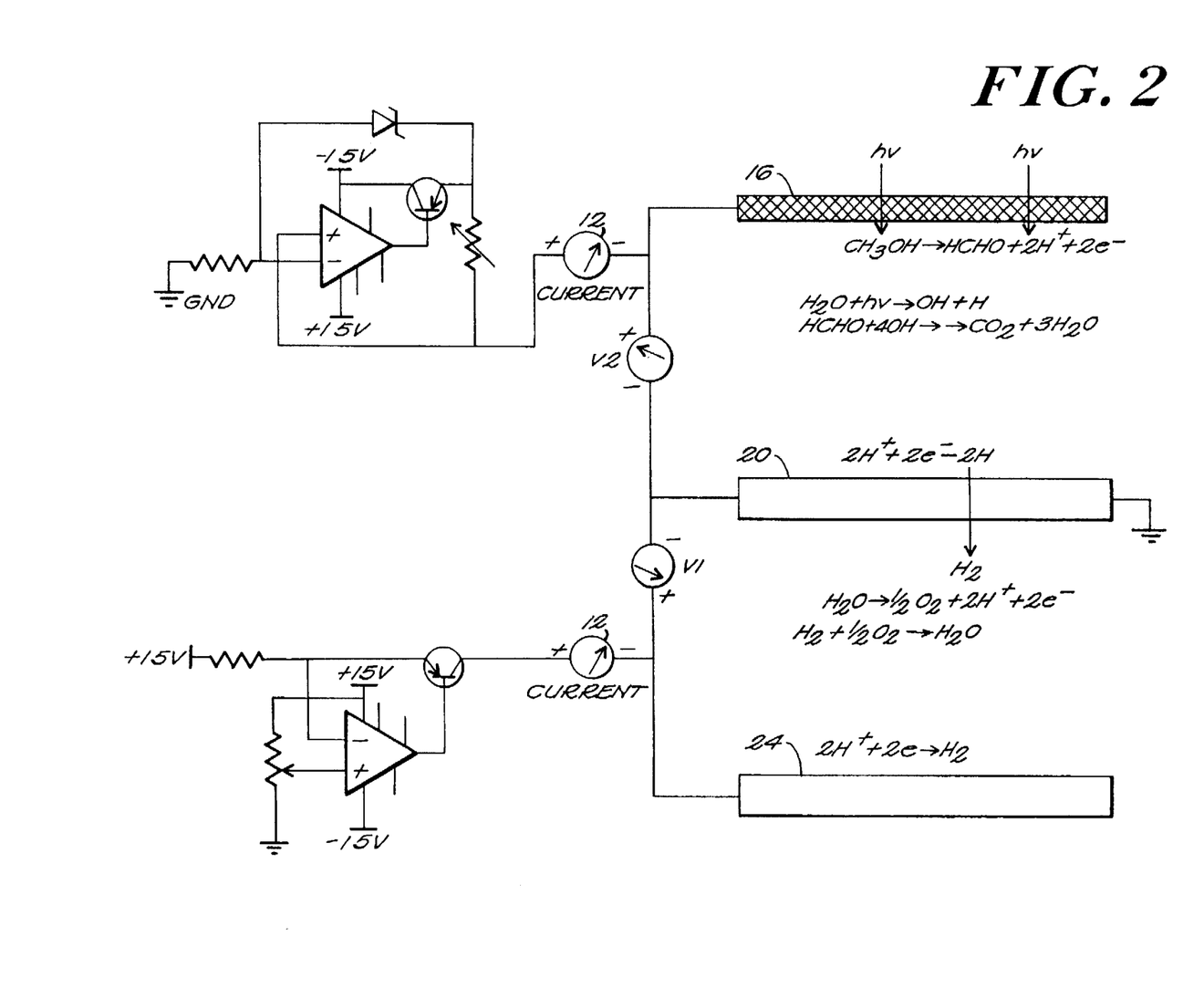
FIG. 2 a schematic diagram of the electrical system of the oxidation reactor of the present invention.

A schematic of the power supply used for these experiments is shown in FIG. 2. The system provides two independent constant current supplies, one for the primary oxidation cell and the second for the electrolysis of water to produce oxygen in the second sample chamber. The cell currents can be independently adjusted, but typically the primary oxidation cell is operated at about 5 mA and the secondary cell is operated at about 10 mA.

FIG. 2 also shows the three electrodes. Electrode #1 is the wire anode 16 of the primary oxidation cell, electrode #2 is the Pd/Ag alloy "bielectrode" 20 of the primary oxidation cell and electrode #3 is the stainless steel pressure plate 24. As shown in FIG. 2, electrode #2 is connected to ground, that is a common current return, not the case of the reactor. Electrode #1 is operated at a sufficiently positive potential so that in the primary oxidation cell, the Pd/Ag alloy (electrode #2) is the cathode and the wire (electrode #1) is the anode. However, electrode #3 is operated at a sufficiently negative potential so that in the secondary electrolysis cell, the stainless steel pressure plate (electrode #3) is the cathode and electrode #2 is the anode.

The system is better understood in terms of the reactions occurring at the electrodes. In the primary oxidation cell, oxidation of the organic compounds and possibly production of "oxygen" from water occurs at the wire electrode #1. Photolytic oxidation of organic compounds can also occur in the primary oxidation cell. Reduction of hydronium ions to form $H_2$ or hydrogen atoms occurs at the Pd/Ag electrode #2. On the secondary electrolysis chamber side of electrode #2, oxidation of water to produce oxygen is the desired reaction, while reduction of hydronium ions to produce $H_2$ occurs at electrode #3.

Since the Pd/Ag alloy electrode is permeable to H atoms, the goal is to have hydrogen produced in the primary oxidation reactor diffuse through the Pd/Ag alloy. At the metal/solution interface of the secondary electrolysis cell, the hydrogen will encounter electrolytically produced oxygen from water and be effectively removed from the system by forming water. Whatever reactions are occurring, the basic idea is to facilitate removal of hydrogen from the primary oxidation cell.

Figure 3:
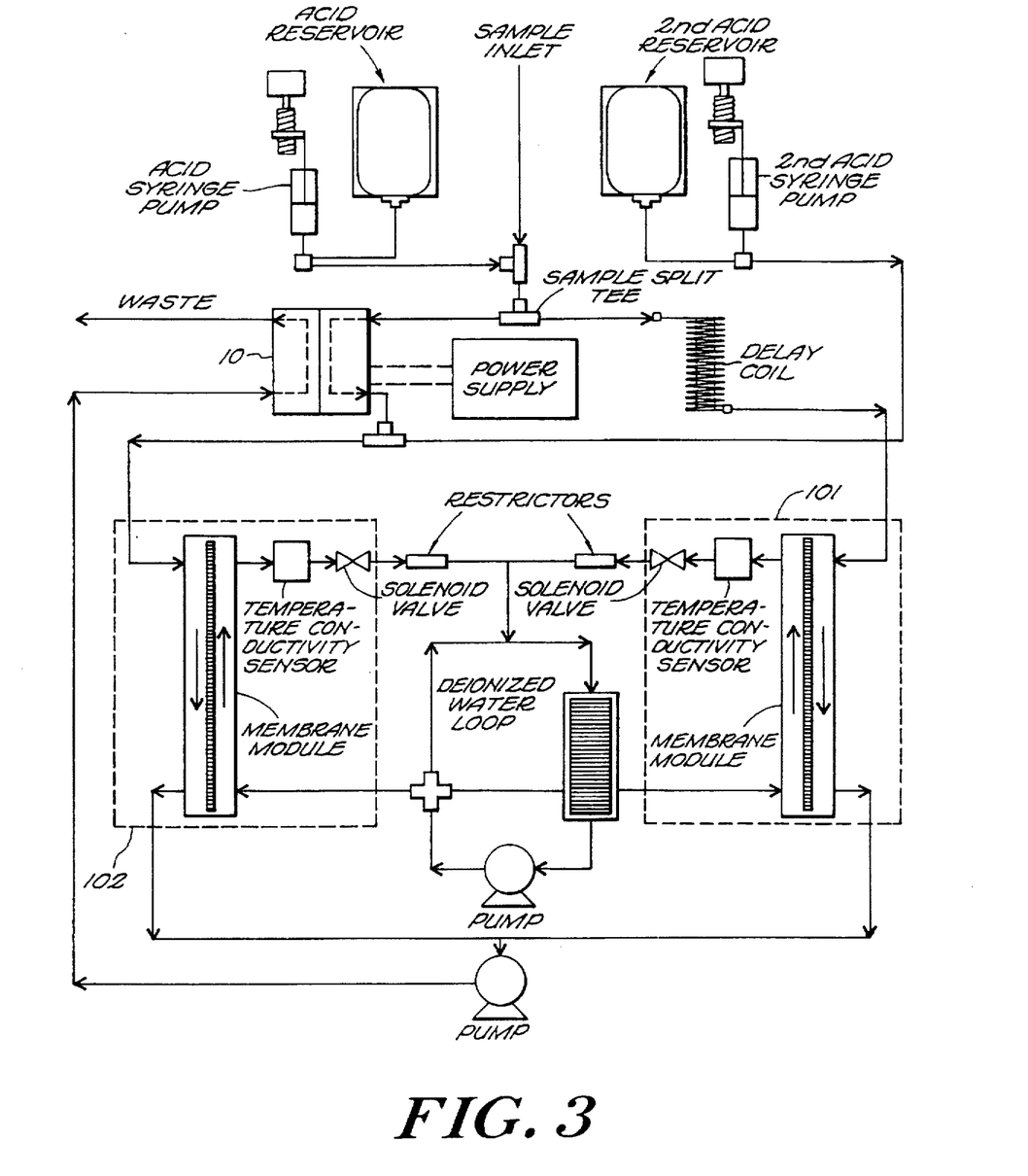
FIG. 3 is a block diagram depicting an embodiment of the present invention for the on-line measurement of both total organic and inorganic carbon concentrations, employment a stream splitting technique.

The oxidation reactor 10 may be used in a TOC detector, such as Sievers Instruments Model 800 TOC analyzer. The normal oxidation reactor is removed from the system and the "Reagentless Oxidation Reactor" is installed. A schematic of the apparatus as so modified is shown in FIG. 3. A variable speed peristaltic sampling pump is used to draw sample into the instrument, typically at a flow rate of 0.28 mL/min. As shown in FIG. 3, the sample stream is split into two channels; Total Inorganic Carbon (TIC) and Total Carbon (TC). In operation, the sample stream is acidified with 6 $MH_3PO_4$ pH<2 and then split. Half of the stream flows through a delay coil (without any oxidation) and into a membrane-based $CO_2$ sensor 101 for the measurement of total inorganic carbon ($HCO_3$ and $CO_3^{-2}$) in the sample. The rest of the sample flows through the oxidation reactor 10 and into a second membrane-based $CO_2$ sensor 102 for the measurement of total carbon content (TC=TIC+TOC). TOC is then computed from the difference. (TOC=TC−TIC).

Operation of the membrane-based $CO_2$ sensors is based on the diffusion of $CO_2$ from the acidified sample stream, across a gas permeable membrane into a thin layer of deionized water. In the deionized water, the $CO_2$ will ionize to form $H^+$ and $HCO_3^-$. As the sample stream flows continuously through the membrane module, the concentration of $CO_2$ on both sides of the membrane will reach an equilibrium. The conductivity of the deionized water can then be measured and the concentration of $CO_2$ in the sample stream determined. As shown in FIG. 3, deionized water is continuously produced by means of circulation pump and a mixed bed of ion exchange resin.

EXAMPLE I

Five compounds were selected for testing with the reactor and are listed in Table I. They represent compounds that are relatively easy to oxidize (methanol, ethanol and KHP), and compounds that should be difficult to oxidize (trichloroethylene and urea).

TABLE I

| Compounds Selected for Testing of Oxidation Reactor | |
|---|---|
| Potassium hydrogen phthalate (KHP) | Methanol |
| Ethanol | Urea |
| Trichloroethylene | |

Standard solutions of the test compounds were prepared in low TOC, deionized water at 10–50 mg/L C. The concentrations of these standard solutions were checked by measurement of TOC using a Sievers Instruments Model 800 TOC Analyzer with UV/persulfate oxidation.

In order to test the new reactor design, some preliminary experiments were performed to establish suitable operating conditions. The reactor was installed in the modified TOC analyzer and thoroughly rinsed with low TOC deionized water to remove any exposed TEFLON brand grease. During this clean-up, the background started at about 3 mg/L TOC and quickly decreased to <100 µg/L within a day.

Figure 4:
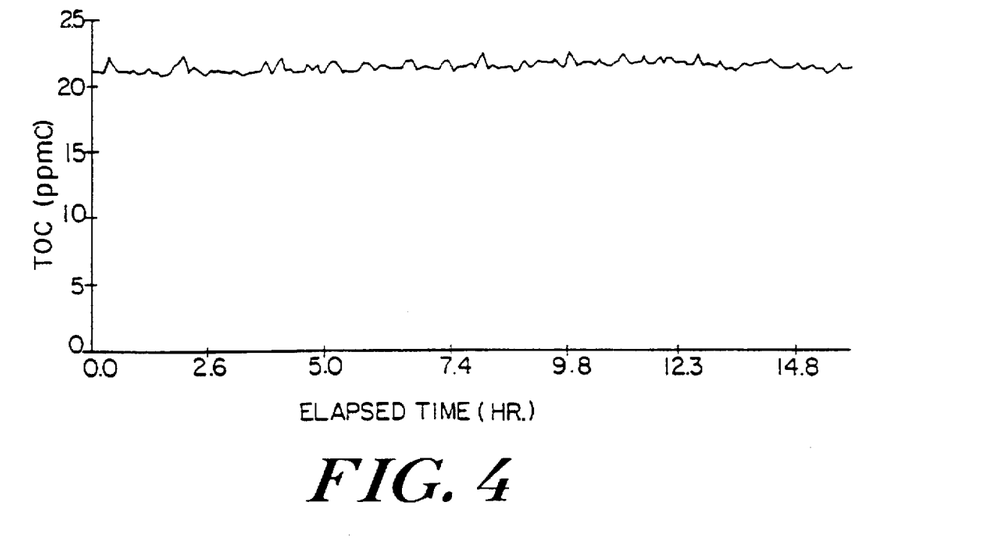
FIG. 4 is a chart showing test results on the oxidation reactor of the present invention.

After the reactor clean-up, the performance of the reactor for the oxidation of a standard solution of potassium hydrogen phthalate (KHP) at ~25 ppm C was determined. A plot of the measured TOC versus time is shown in FIG. 4. The purpose of this experiment was simply to establish operating conditions for the electrolysis cells, but as shown in FIG. 4, the reactor operated for 16 hours without any significant decrease in oxidation efficiency.

In the experimental set-up, the reactor is not enclosed or thermostated, but heat from the UV lamps and the electrolysis cells increases the temperature of the outside of the reactor to >30° C. All of the preliminary experiments were performed at these elevated temperatures.

Figure 5:
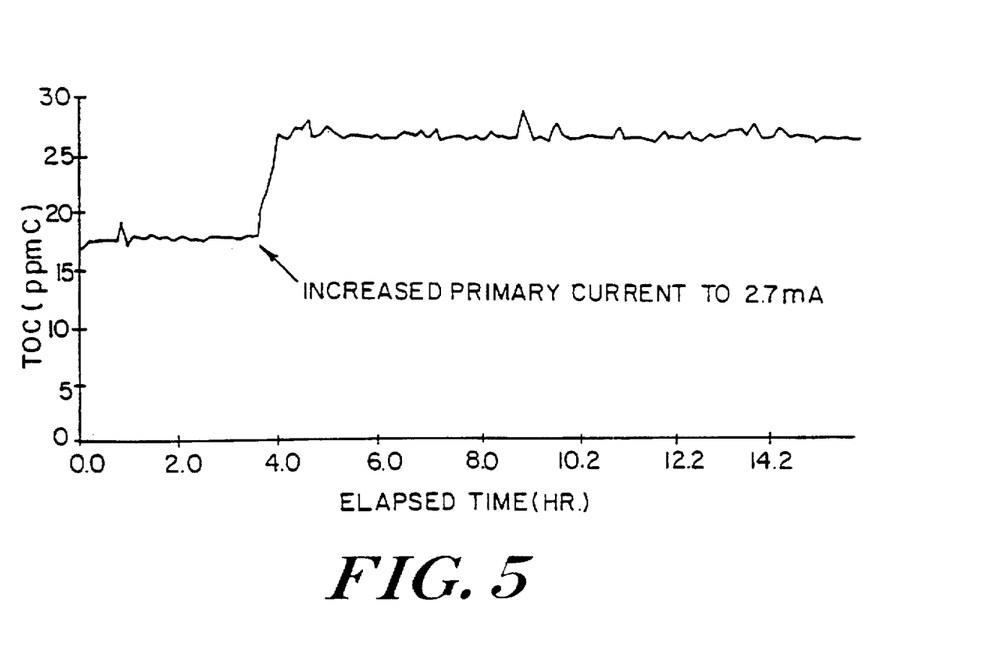
FIG. 5 is a chart showing test results on the oxidation reactor of the present invention.

The oxidation efficiency for a standard solution of KHP (28.6 mg/L C) was determined as a function of applied current and the results from this test are shown in FIG. 5. Initially, the primary oxidation cell was operated at an applied current of 1.7 mA and the secondary cell operated at 3 mA. The residence time of the sample in the reactor was 5.6 minutes. Under these conditions, the oxidation efficiency was only 63%, but no decrease in performance was observed. The current for the primary cell was then increased to 2.7 mA and the secondary cell current increased to 4.1 mA. The oxidation efficiency at the higher current increased to 93% and the oxidation efficiency remained relatively constant at the higher current for about 12 hours of continuous operation.

EXAMPLE II

A possible obstacle to the complete oxidation of organic to $CO_2$ is the reduction of $CO_2$ in the reactor in the presence of unremoved $H_2$. When a standard solution of $Na_2CO_3$ was passed through an earlier reactor design that did not have the secondary electrolysis chamber, the response of the $CO_2$ sensor was 10–15% lower than expected, and it was determined that $CO_2$ was being electrolytically reduced in the reactor. Therefore, an experiment was performed with the present invention to analyze a 25 mg/L C solution of $Na_2CO_3$. Analysis of the solution with the electrolysis cells and UV lamps off gave an average TC value of 25.2 mg/L. When the electrolysis cells were turned on, but with the UV lamps off, the average TC value was 25.3 mg/L. Analysis of this solution with both electrolysis and UV lamps on gave an average TC value of 24.9 mg/L. The results from these experiments suggest that reduction of $CO_2$ is not occurring to any significant degree in the new reactor design. The more effective hydrogen removal from the primary oxidation reactor using the secondary electrolysis chamber for hydrogen removal prevented the reduction of $CO_2$ in the primary oxidation reactor.

EXAMPLE III

A preliminary investigation of the effect of residence time in the reactor (i.e. sample flow rate) on the oxidation efficiency was performed. The 30.5 mg/L KHP standard was analyzed for about 9 hours with a reactor residence time of 5.5 minutes (primary current=4.6 mA, secondary current=10 mA), then the flow rate was decreased to give a residence time of 7.2 min. using the same reactor currents. The rate of addition of acid was also changed to maintain the same pH for the sample stream at the lower sample flow rates. At the shorter residence time (5.5 min.) the oxidation efficiency was 95% (TOC=29.6±0.2 mg/L). Increasing the residence time to 7.2 minutes gave an average oxidation efficiency of 99.5% (TOC=30.4±0.3 mg/L).

Figure 6:
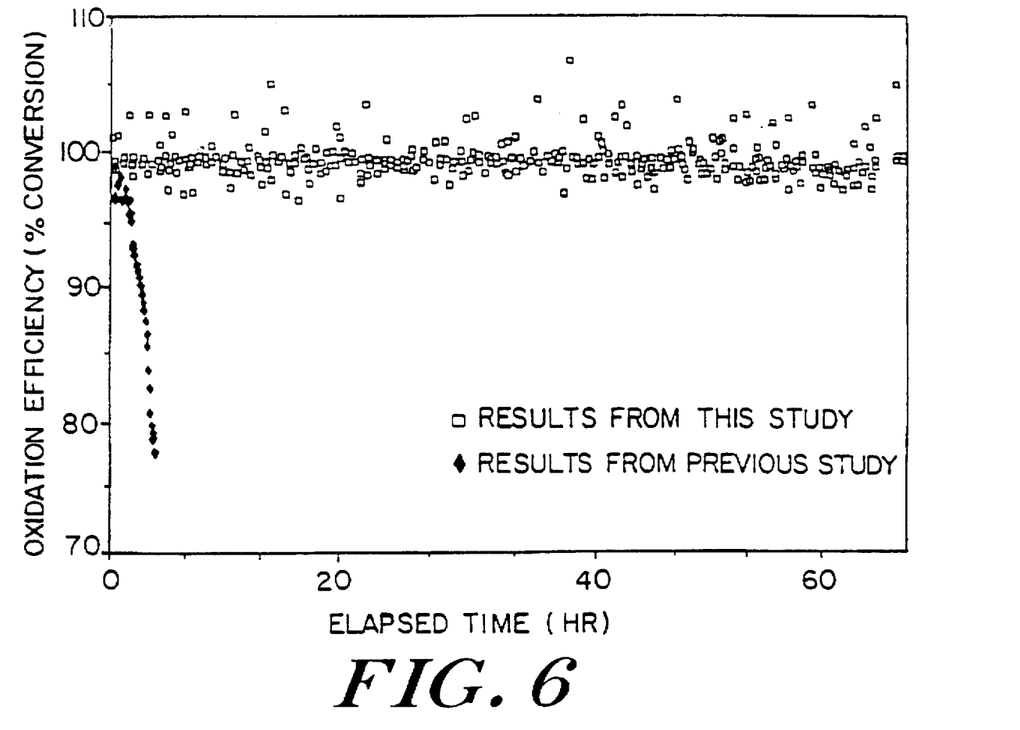
FIG. 6 is a chart showing the oxidation efficiency of the oxidation reactor of the present invention over time.

To determine if this higher oxidation efficiency at the longer residence time could be sustained, the 30.5 mg/L KHP standard was run for about 64 hours (primary current =4.6 mA, secondary current=10 mA, residence time=7.2 min. ) and the results are shown in FIG. 6, along with the best results achieved in a previous study using no secondary electrolysis hydrogen removal chamber.

The oxidation efficiency of the new reactor was stable for this 64 hour test, with an average efficiency of 99.3% (TOC=30.3±0.3 mg/L). In contrast, the best results from a previous study showed stable performance for only about 1.5 hours, followed by a precipitous drop-off in oxidation efficiency.

The improved performance of the new reactor design is most likely due to a combination of factors. The wire mesh anode has a significantly larger surface area than the anode used in the original reactor design. The large anode area results in improved electrolytic oxidation. The new reactor design also permits more efficient removal of hydrogen from the reactor. In the new design, hydrogen production appears to be distributed more uniformly across the Pd/Ag alloy. Finally, the use of the secondary electrolysis cell improves the removal of hydrogen from the Pd/Ag alloy preventing hydrogen build-up in the primary oxidation electrolysis chamber.

EXAMPLE IV

The efficiency of the reactor for the oxidation of a 45.7 mg/L C solution of ethanol was determined at three different flow rates and the results from this test are shown in Table II. All experiments were performed with a primary current of 5.1 mA and a secondary current of 11.4 mA. In contrast with the experiments described above, a fan was used to cool the outside of the reactor to ~27° C. Oxidation efficiency increased with increasing residence time, however the oxidation efficiency was reduced at the lower reactor temperature.

TABLE II

Oxidation Efficiency versus Reactor Residence Time for 45.7 ppm C Ethanol at 27° C.

| Reactor Residence Time (min) | Oxidation Efficiency |
|---|---|
| 10 | 63% |
| 15 | 87% |
| 20 | 97% |

EXAMPLE V

As noted above, lower oxidation efficiency was observed when the reactor was cooled. The rate of most chemical reactions will increase as the temperature is raised, typically doubling for each 10° C. increase in temperature. Thus, one would expect higher oxidation efficiencies at higher temperatures. The situation regarding removal of hydrogen from the reactor using the Pd/Ag alloy is more complicated. The diffusion of hydrogen atoms through Pd and Pd/Ag alloys increases with increasing temperature. However, the solubility of hydrogen in these materials decreases with increasing temperatures. Calculations indicate that overall permeation of hydrogen should increase with increasing temperatures and therefore a series of experiments were performed to determine if better efficiencies could be obtained at higher reactor temperatures.

Figure 7:
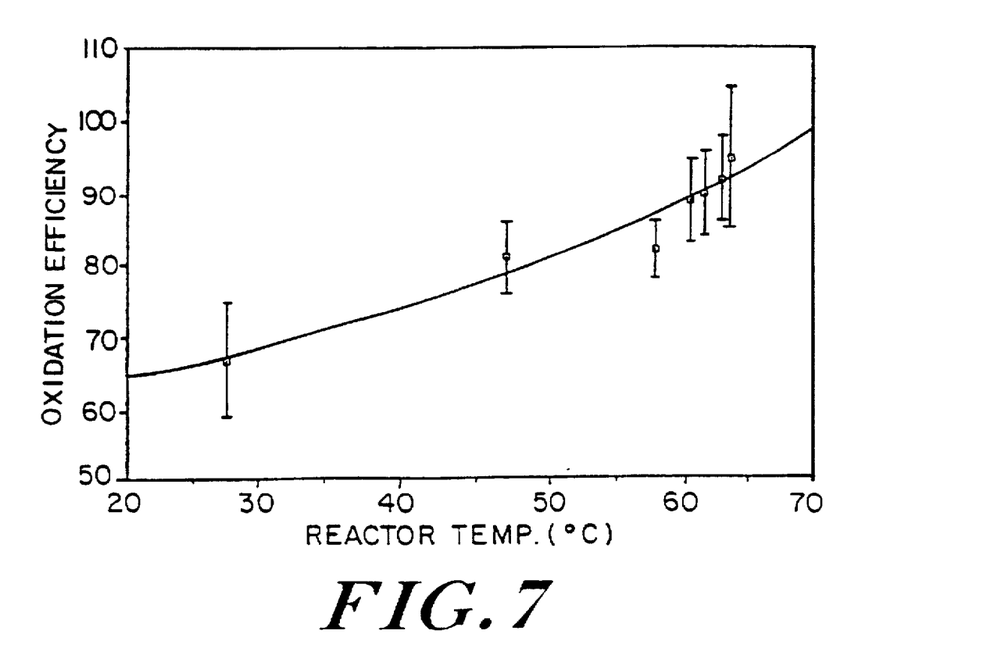
FIG. 7 is a chart showing the oxidation efficiency of the oxidation reactor of the present invention compared to reactor temperature.

For these experiments, a fan was used initially to cool the reactor, with applied currents of 5.1 mA for the primary and 11 mA for the secondary cell, with a residence time of 15 min. The fan was then turned off and the temperature of the reactor allowed to rise. The reactor was not thermostated, rather the temperature of the outside of the reactor was monitored and an "average" temperature and TOC determined as the reactor warmed. Finally, the reactor was insulated to obtain temperatures above 60° C. The results from this experiment are shown in FIG. 7.

The oxidation efficiency increased from 75% to 95% as the temperature of the reactor increased. The error bars are ±one standard deviation and the wide range in the measurements is most likely due to changing temperatures during the course of this experiment.

The result from this experiment indicates that the best oxidation efficiency will be obtained at higher temperatures. The present design does not permit heating of the reactor, but a temperature of ~60° C. can be maintained by insulating the reactor.

Using the insulated reactor, one can determine the oxidation efficiency as a function of reactor residence time for three of the test compounds, trichloroethylene, urea and methanol. These experiments were performed at a 5 mA current for the primary cell and 11 mA for the secondary cell. The results from these tests are shown in Table III. Using a 20 minute residence time and a reactor temperature of ~600° C., an oxidation efficiency of 96% was achieved for urea and 97% for trichloroethylene. For methanol, an 88% oxidation efficiency was obtained for a 7 min. reactor residence time and 99% oxidation was obtained at 20 min. residence time.

If one assumes that the rate of the oxidation reactions is independent of the concentration of oxidizing agents then the rate of the oxidation is simply rate of oxidation=$k^1$ [organic compound] where $K^1$ is a pseudo first order rate constant. Using the results from Table III, one can calculate the pseudo first order rate constant and these values are shown in Table IV.

The pseudo first order rate constant for ethanol and urea at 27° C. are larger than the recently reported oxidation rate constants using ozone and hydrogen peroxide for large scale oxidation of organic compounds in water. For the oxidation of urea, Verostko et al., measured $k^1$ of 0.003/min. The 0.06/min. value obtained in this study using the present invention reflects the rapid oxidation that can be achieved using combined photolytic and electrolytic oxidation at elevated temperatures.

At the higher reactor temperature, an approximately three fold increase in the rate of the reaction was observed. The important factor in using this reactor for TOC measurements is the residence time in the reactor required to achieve complete oxidation. Based on half life measurements, increasing the reactor temperature greatly decreased the amount of time required for 50% oxidation and operating at the higher temperature provides a more reasonable measurement time for TOC analysis.

TABLE III

Performance of Oxidation Reactor at Elevated Temperatures

| Compound | Oxidation Efficiency Residence Time (minutes) | | | |
|---|---|---|---|---|
| | 7.2 | 10 | 15 | 20 |
| Urea (42.5 ppm C) | — | 58% | 70% | 96% |
| Trichloroethylene (20.2 ppm C) | — | — | — | 97% |
| Methanol (46.2 ppm C) | 88% | 97% | 98% | 99% |

TABLE IV

Pseudo First Order Rate Constants and Half Lifes

| Compound | $k^1$ (min.$^{-1}$) | $t_{1/2}$(min.)* |
|---|---|---|
| Urea (60° C.) | 0.06 | 12 |
| Methanol (60° C.) | 0.13 | 5 |
| Ethanol (27° C.) | 0.08 | 8 |
| Urea (27° C.) | 0.02 | 35 |

*$t_{1/2} = (1/k^1) \ln 2$

What is claimed is:

1. An apparatus for the measurement of carbon compounds in an aqueous sample in a sample stream, comprising:
   (a) a reactor for the conversion of organic compounds in the sample stream to carbon dioxide, said reactor comprising:
      (i) a first chamber for the conversion of organic compounds into carbon dioxide and a second chamber, separated from the first chamber by a hydrogen-permeable, electrically-conductive material; further wherein said first and second chambers each define adjacent serpentine channels separated by said hydrogen-permeable, electrically-conductive material; and
      (ii) means for electrically connecting said first and second chambers to a power supply so as to establish a first electrical potential across said first chamber between a first chamber anode means and said hydrogen-permeable, electrically-conductive material and a second electrical potential across said second chamber between said hydrogen-permeable, electrically-conductive material and second chamber cathode means; and,
   (b) a carbon dioxide sensor in communication with the oxidation reactor to measure the carbon dioxide to determine the carbon concentration in the sample stream.

2. An apparatus for the measurement of carbon compounds in an aqueous sample in a sample stream, said apparatus comprising:
   (a) a reactor for the conversation of organic compounds in the sample stream to carbon dioxide, said reactor comprising:
      (i) a first chamber for the conversion of organic compounds into carbon dioxide and a second chamber separated from the first chamber by a hydrogen-permeable, electrically-conductive material;
      (ii) an ultraviolet light source to irradiate said first chamber with ultraviolet light;
      (iii) a first chamber electrolysis cell having a first chamber electrolysis cell anode between the sample stream in the first chamber and the ultraviolet light source, said first chamber anode being able to transmit at least some ultraviolet light; and, (iv) means for electrically connecting said first and second chambers to a power supply so as to establish a first electrical potential across said first chamber between said first chamber anode and said hydrogen-permeable, electrically-conductive material and a second electrical potential across said second chamber between said hydrogen-permeable, electrically-conductive material and another electrically-conductive surface of said second chamber; and, (b) a carbon dioxide sensor in communication with the oxidation reactor to measure the carbon dioxide to determine the carbon concentration in the sample stream.

3. The apparatus of claim 2, wherein said hydrogen-permeable electrically conductive material is a sheet selected from the group consisting of palladium, palladium alloy, titanium and titanium alloy.

4. The apparatus of claim 2, wherein the ultraviolet light source produces at least some light having a wavelength less than 254 nm.

5. The apparatus of claim 4, wherein the ultraviolet light source is chosen from the group consisting of mercury vapor lamps, xenon-doped mercury lamps, krypton chloride excimer lamps and xenon excimer lamps.

6. The apparatus of claim 2, wherein the first chamber electrolysis cell anode is an electrically conductive screen.

7. The apparatus of claim 6 wherein the electrically conductive screen includes a mesh selected from the group consisting of titanium, platinum, and gold.

8. The apparatus of claim 2, wherein the carbon dioxide sensor has an outlet in fluid communication with the reactor second chamber.

9. A reactor for the conversion of organic compounds in a sample stream to carbon dioxide, comprising a first chamber for the conversion of organic compounds into carbon dioxide and a second chamber separated from the first chamber by a hydrogen-permeable, electrically-conductive material; further wherein:

(a) said first chamber includes a first chamber electrolysis cell having a first chamber electrolysis cell anode for the production of oxygen and a first chamber electrolysis cell cathode for the production of hydrogen;

(b) said second chamber includes a second chamber electrolysis cell having a second chamber electrolysis cell anode for the production of oxygen and a second chamber electrolysis cell cathode; wherein said first chamber electrolysis cell cathode and said second chamber electrolysis cell anode are said hydrogen-permeable, electrically-conductive material; and (c) said first chamber and said second chamber each define adjacent serpentine channels separated by said hydrogen-permeable, electrically-conductive material.

10. A reactor for the conversion of organic compounds in a sample stream to carbon dioxide comprising:

(a) a first chamber for the conversion of organic compounds into carbon dioxide and a second chamber separated from the first chamber by a hydrogen-permeable, electrically-conductive material;

(b) an ultraviolet light source to irradiate said first chamber with ultraviolet light;

(c) a first chamber electrolysis cell having a first chamber electrolysis cell anode between the sample stream in the first chamber and the ultraviolet light source, said first chamber anode being able to transmit at least some ultraviolet light; and, (d) means for electrically connecting said first and second chambers to a power supply so as to establish a first electrical potential across said first chamber between said first chamber anode and said hydrogen-permeable, electrically-conductive material and a second electrical potential across said second chamber between said hydrogen-permeable, electrically-conductive material and another electrically-conductive surface of said second chamber.

11. The reactor of claim 10, wherein said hydrogen-permeable, electrically conductive material is a sheet selected from the group consisting of palladium, palladium alloys, titanium and titanium alloys.

12. The reactor of claim 10, wherein said ultraviolet light source produces at least some light having a wavelength less than 254 nm.

13. The reactor of claim 10, wherein the ultraviolet light source is chosen from the group consisting of mercury vapor lamps, xenon-doped mercury lamps, krypton chloride excimer lamps and xenon excimer lamps.

14. The reactor of claim 10, wherein the first chamber electrolysis cell anode is an electrically conductive screen.

15. The reactor of claim 14, wherein the electrically conductive screen includes a mesh selected from the group consisting of titanium, platinum, and gold.

16. An apparatus for converting compounds in an aqueous sample to their respective oxides, comprising a reactor having a first chamber for the conversion of said compounds into their oxides and a second chamber separated from the first chamber by a selectively hydrogen-permeable, electrically-conductive membrane wherein said membrane is inorganic and wherein hydrogen permeates said membrane; further wherein:

(a) said reactor first chamber includes a first chamber electrolysis cell having a first chamber electrolysis cell anode for the production of oxygen and a first chamber electrolysis cell cathode for the production of hydrogen to pass at least in part through the selectively hydrogen-permeable, electrically-conducive material into the second chamber;

(b) said second chamber includes a second chamber electrolysis cell having a second chamber electrolysis cell anode for the oxidation of at least part of said hydrogen passed through the hydrogen-permeable, electrically-conductive material and a second chamber electrolysis cell cathode; wherein said selectively hydrogen-permeable, electrically-conductive material is a bi-polar electrode forming said first chamber electrolysis cell cathode and said second chamber electrolysis cell anode; and (c) said first chamber and said second chamber each define adjacent serpentine channels separated by said selectively hydrogen-permeable, electrically-conductive material.

17. An apparatus for converting organic compounds in an aqueous sample to their respective oxides, said apparatus comprising a reactor for the conversion of compounds in a sample to their respective oxides, said reactor comprising:

(a) a first chamber for the conversion of said compounds into their respective oxides and a second chamber separated from the first chamber by a selectively hydrogen-permeable, electrically-conductive membrane wherein said membrane is inorganic and wherein hydrogen which permeates said membrane is oxidized at least in part;

(b) an ultraviolet light source to irradiate said first chamber with ultraviolet light;

(c) a first chamber electrolysis cell having a first chamber electrolysis cell anode between the sample stream in the first chamber and the ultraviolet light source, said first chamber anode being able to transmit at least some ultraviolet light; and, (d) means for electrically connecting said first and second chambers to a power supply so as to establish a first electrical potential across said first chamber between said first chamber anode and said hydrogen-permeable, electrically-conductive material and a second electrical potential across said second chamber between said hydrogen-permeable, electrically-conductive material and another electrically-conductive surface of said second chamber.

18. The apparatus of claim 17, wherein said selectively hydrogen-permeable, electrically conductive membrane is selected from a group consisting of palladium, palladium alloys, titanium and titanium alloys.

19. The apparatus of claim 17, wherein the ultraviolet light source produces at least some light having a wavelength less than 254 nm.

20. The apparatus of claim 19, wherein the ultraviolet light source is chosen from the group consisting of mercury vapor lamps, xenon-doped mercury lamps, krypton chloride excimer lamps and xenon excimer lamps.

21. The apparatus of claim 17, wherein the first chamber electrolysis cell anode is an electrically conductive screen.

22. The apparatus of claim 21, wherein the electrically conductive screen includes mesh selected from the group consisting of titanium, platinum, and gold.

23. An apparatus for the measurement of carbon compounds in an aqueous sample, said apparatus comprising:

(a) a reactor for substantially completely converting the organic compounds in a portion of said sample to carbon dioxide, said reactor comprising:

(i) a first electrolysis cell comprising first anode means, first cathode means, and a first liquid flow path for flowing substantially all of said portion therebetween;

(ii) a second electrolysis cell comprising second anode means, second cathode means, and a second liquid flow path for passing aqueous solution therebetween, further wherein said first and second electrolysis cells are separated by an electrically-conductive member consisting essentially of a selectively hydrogen-permeable, water-impermeable material; and (iii) means for electrically connecting said first anode means, said second cathode means, and said hydrogen-permeable, electrically-conductive member to power supply means so as to establish a first electrical potential across said first electrolysis cell whereby said hydrogen-permeable, electrically-conductive member can function as said first cathode means, and so as to establish a second electrical potential across said second electrolysis cell whereby said hydrogen-permeable, electrically-conductive member can also function as said second anode means; and (b) a carbon dioxide sensor in communication with the oxidation reactor to measure the carbon dioxide to determine the carbon concentration in the sample stream.

24. The apparatus of claim 23, wherein the reactor includes an ultraviolet light source to irradiate said first electrolysis cell with ultraviolet light to convert said organic compounds to carbon dioxide.

25. An apparatus according to claim 23 wherein said hydrogen-permeable, electrically-conductive member is inorganic.

26. An apparatus according to claim 25 wherein said hydrogen-permeable, electrically-conductive member is selected from the group consisting of palladium, palladium alloys, titanium, and titanium alloys.

27. A reactor apparatus for substantially completely converting the organic compounds in a portion of an aqueous sample to carbon dioxide, said apparatus comprising:

(a) a first electrolysis cell comprising first anode means, first cathode means, and a first liquid flow path for flowing a substantial part of said portion therebetween;

(b) a second electrolysis cell comprising second anode means, second cathode means, and a second liquid flow path for passing aqueous liquid therebetween, further wherein said first and second electrolysis cells are separated by an electrically-conductive member consisting essentially of a selectively hydrogen-permeable, water-impermeable material;

(c) means for electrically connecting said first anode means, said second cathode means, and said hydrogen-permeable, electrically-conductive member to power supply means so as to establish a first electrical potential across said first electrolysis cell whereby said hydrogen-permeable, electrically-conductive member can function as said first cathode means, and so as to establish a second electrical potential across said second electrolysis cell whereby said hydrogen-permeable, electrically-conductive member can also function as said second anode means; and (d) a carbon dioxide sensor in communication with said first electrolysis cell to determine the carbon concentration of said portion coming from said first electrolysis cell.

28. The reactor apparatus of claim 27, further comprising an ultraviolet light source to irradiate said first electrolysis cell with ultraviolet light to promote the conversion of organic compounds to carbon dioxide.

29. The reactor apparatus of claim 28 wherein said ultraviolet light source produces at least some light having a wavelength less than about 254 nm.

30. The reactor apparatus of claim 28 wherein said ultraviolet light source is chosen from the group consisting of mercury vapor lamps, xenon-doped mercury lamps, krypton chloride excimer lamps and xenon excimer lamps.

31. The reactor apparatus according to claim 27 wherein said hydrogen-permeable, electrically-conductive member is inorganic.

32. The reactor apparatus according to claim 31 wherein said hydrogen-permeable, electrically-conductive member is selected from the group consisting of palladium, palladium alloys, titanium, and titanium alloys.

33. An apparatus for converting compounds in a portion of an aqueous sample to their respective oxides, said apparatus comprising:

(a) a first electrolysis cell comprising first anode means, first cathode means, and a first liquid flow path for flowing substantially all of said portion therebetween;

(b) a second electrolysis cell comprising second anode means, second cathode means, and a second liquid flow path for passing aqueous liquid therebetween, further wherein said first and second electrolysis cells are separated by an electrically-conductive member consisting essentially of a selectively hydrogen-permeable membrane;

(c) means for electrically connecting said first anode means, said second means, and said hydrogen-permeable, electrically-conductive membrane to power supply means so as to establish a first electrical potential across said first electrolysis cell whereby said hydrogen-permeable, electrically-conductive member can function as said first cathode means, and so as to establish a second electrical potential across said second electrolysis cell whereby said hydrogen-permeable, electrically-conductive membrane can also function as said second anode means; and (d) a carbon dioxide sensor in communication with said first electrolysis cell to determine the carbon concentration of said portion coming from said first electrolysis cell.

34. The apparatus of claim 33 further comprising an ultraviolet light source to irradiate said first electrolysis cell with ultraviolet light to promote converting said compounds to their oxides.

35. An apparatus according to claim 33 wherein said selectively hydrogen-permeable membrane is water-impermeable.

36. An apparatus according to claim 33 wherein said selectively hydrogen-permeable membrane is inorganic.

37. An apparatus according to claim 36 wherein said selectively hydrogen-permeable membrane is selected from the group consisting of palladium, palladium alloys, titanium, and titanium alloys.

38. A reactor comprising:

(a) a first chamber defining a first liquid flow path extending from an input port to an output port, (b) a second chamber defining a second liquid flow path extending from an input port to an output port, wherein said first and second chambers include a common electrically-conductive, hydrogen-permeable sheet member defining a lateral boundary of said first and second flow paths, and wherein said first chamber includes an electrically-conductive first element at or adjacent to a lateral boundary of said first flow path opposite to said sheet member, said first element being electrically isolated from said sheet member and able to transmit at least some ultraviolet light, wherein said second chamber includes a second electrically-conductive element at or adjacent to a lateral boundary of said second flow path opposite said sheet member, said second element being electrically isolated from said sheet member, and further comprising:

(c) means for coupling a power source between said first element and said sheet member for establishing said first element as an anode relative to said sheet member, and (d) means for coupling a power source between said sheet member and said second element for establishing said second element as a cathode relative to said sheet member, and (e) an ultraviolet light source positioned outside said first chamber and adjacent to said first element whereby ultraviolet light is coupled into said first chamber.

39. A reactor apparatus for substantially completely converting the organic compounds in a portion of an aqueous sample to carbon dioxide, said apparatus comprising:

(a) a first electrolysis cell comprising first anode means, first cathode means, and a first liquid flow path for flowing a substantial part of said portion therebetween;

(b) an ultraviolet light source to irradiate said first electrolysis cell with ultraviolet light to promote the conversion of organic compounds to carbon dioxide, further wherein said first anode means is located between said ultraviolet light source and said aqueous sample in said first electrolysis cell, said first anode means being able to transmit at least some ultraviolet light;

(c) a second electrolysis cell comprising second anode means, second cathode means, and a second liquid flow path for passing aqueous liquid therebetween, further wherein said first and second electrolysis cells are separated by an electrically-conductive member consisting essentially of a selectively hydrogen-permeable, water-impermeable material; and (d) means for electrically connecting said first anode means, said second cathode means, and said hydrogen-permeable, electrically-conductive member to power supply means so as to establish a first electrical potential across said first electrolysis cell whereby said hydrogen-permeable, electrically-conductive member can function as said first cathode means, and so as to establish a second electrical potential across said second electrolysis cell whereby said hydrogen-permeable, electrically-conductive member can also function as said second anode means.

40. A reactor apparatus for substantially completely converting the organic compounds in a portion of an aqueous sample to carbon dioxide, said apparatus comprising:

(a) a first electrolysis cell comprising first anode means, first cathode means, and a first liquid flow path for flowing a substantial part of said portion therebetween, further wherein said first anode means comprises an electrically conductive screen;

(b) a second electrolysis cell comprising second anode means, second cathode means, and a second liquid flow path for passing aqueous liquid therebetween, further wherein said first and second electrolysis cells are separated by an electrically-conductive member consisting essentially of a selectively hydrogen-permeable, water-impermeable material; and (c) means for electrically connecting said first anode means, said second cathode means, and said hydrogen-permeable, electrically-conductive member to power supply means so as to establish a first electrical potential across said first electrolysis cell whereby said hydrogen-permeable, electrically-conductive member can function as said first cathode means, and so as to establish a second electrical potential across said second electrolysis cell whereby said hydrogen-permeable, electrically-conductive member can also function as said second anode means.

41. The reactor apparatus of claim 40, wherein said electrically conductive screen comprises a mesh selected from the group consisting of titanium, platinum, and gold.

42. An apparatus for converting compounds in a portion of an aqueous sample to their respective oxides, said apparatus comprising:

(a) a first electrolysis cell comprising first anode means, first cathode means, and a first liquid flow path for flowing a substantial part of said portion therebetween, further wherein said first anode means comprises an electrically conductive screen;

(b) a second electrolysis cell comprising second anode means, second cathode means, and a second liquid flow path for passing aqueous liquid therebetween, further wherein said first and second electrolysis cells are separated by an electrically-conductive member consisting essentially of a selectively hydrogen-permeable membrane; and, (c) means for electrically connecting said first anode means, said second cathode means, and said hydrogen-permeable, electrically-conductive membrane to power supply means so as to establish a first electrical potential across said first electrolysis cell whereby said hydrogen-permeable, electrically-conductive member can function as said first cathode means, and so as to establish a second electrical potential across said second electrolysis cell whereby said hydrogen-permeable, electrically-conductive membrane can also function as said second anode means.

43. An apparatus for converting compounds in a portion of an aqueous sample to their respective oxides, said apparatus comprising:

(a) a first electrolysis cell comprising first anode means, first cathode means, and a first liquid flow path for flowing a substantial part of said portion therebetween;

(b) an ultraviolet light source to irradiate said first electrolysis cell with ultraviolet light to promote the conversion of organic compounds to carbon dioxide, further wherein said first anode means is located between said ultraviolet light source and said aqueous sample in said first electrolysis cell, said first anode means being able to transmit at least some ultraviolet light;

(b) a second electrolysis cell comprising second anode means, second cathode means, and a second liquid flow path for passing aqueous liquid therebetween, further wherein said first and second electrolysis cells are separated by an electrically-conductive member consisting essentially of a selectively hydrogen-permeable membrane; and, (c) means for electrically connecting said first anode means, said second cathode means, and said hydrogen-permeable, electrically-conductive membrane to power supply means so as to establish a first electrical potential across said first electrolysis cell whereby said hydrogen-permeable, electrically-conductive member can function as said first cathode means, and so as to establish a second electrical potential across said second electrolysis cell whereby said hydrogen-permeable, electrically-conductive membrane can also function as said second anode means.

* * * * *